United States Patent
Maciejewski et al.

(10) Patent No.: US 10,342,453 B2
(45) Date of Patent: Jul. 9, 2019

(54) CATCH DEVICE AND SHELL LINER FOR A MEDICAL IMAGING APPARATUS

(71) Applicant: Siemens Healthcare GmbH, Erlangen (DE)

(72) Inventors: Bernd Maciejewski, Markt Erlbach (DE); Jian Hua Pei, Shenzhen (CN); Wen Qiang You, Shenzhen (CN)

(73) Assignee: Siemens Healthcare GmbH, Erlangen (DE)

( * ) Notice: Subject to any disclaimer, the term of this patent is extended or adjusted under 35 U.S.C. 154(b) by 345 days.

(21) Appl. No.: 15/147,111

(22) Filed: May 5, 2016

(65) Prior Publication Data

US 2016/0327621 A1 Nov. 10, 2016

(30) Foreign Application Priority Data

May 7, 2015 (CN) .................... 2015 2 0291515 U

(51) Int. Cl.
  *F16D 41/00* (2006.01)
  *A61B 5/055* (2006.01)
  *G01R 33/28* (2006.01)
  *G01R 33/38* (2006.01)

(52) U.S. Cl.
  CPC .............. *A61B 5/055* (2013.01); *G01R 33/28* (2013.01); *G01R 33/3802* (2013.01)

(58) Field of Classification Search
  CPC ...... B65H 2301/33312; B65H 2402/31; B65H 2404/1431; G01R 33/3802; A61B 5/055
  See application file for complete search history.

(56) References Cited

U.S. PATENT DOCUMENTS

| | | | | |
|---|---|---|---|---|
| 3,577,840 | A * | 5/1971 | Buberniak | E05D 11/1014 16/332 |
| 3,722,030 | A * | 3/1973 | Smith | E05D 11/1014 16/303 |
| 3,728,757 | A * | 4/1973 | Lloyd | E05D 11/1014 16/303 |
| 4,411,511 | A * | 10/1983 | Ariyama | B65H 29/56 271/307 |
| 5,493,967 | A * | 2/1996 | Malin | G07B 17/00508 101/109 |
| 6,690,579 | B1 * | 2/2004 | Ribeiro | G06F 1/1613 361/728 |

(Continued)

*Primary Examiner* — Alesa Allgood
(74) *Attorney, Agent, or Firm* — Schiff Hardin LLP

(57) ABSTRACT

A catch device and a shell liner for a medical imaging apparatus and a magnetic resonance imaging (MRI) apparatus that has an elastic arm, the elastic arm having a clamping portion, two bending portions located on two sides of the clamping portion and two end portions formed by extension of the ends of the two bending portions away from the clamping portion, the two end portions being used for being fixed to a liner of the first shell; and at least one roller, the roller being rotatably sheathed on the clamping portion of the elastic arm and clamping an edge of the second shell to the liner of the first shell by using an elastic force of the elastic arm, and an axial direction of the roller is parallel to the liner of the first shell and the edge of the second shell. The catch device achieves a simple and firm connection between apparatus shells, and meets requirements for a pleasing appearance and convenient application and maintenance.

4 Claims, 5 Drawing Sheets

(56) References Cited

U.S. PATENT DOCUMENTS

| | | | |
|---|---|---|---|
| 9,404,517 B2* | 8/2016 | Kasper | G01R 33/28 |
| 2010/0038517 A1* | 2/2010 | Home | B60B 33/0063 248/646 |

\* cited by examiner

CATCH DEVICE AND SHELL LINER FOR A MEDICAL IMAGING APPARATUS

BACKGROUND OF THE INVENTION

Field of the Invention

The present invention concerns the field of medical devices, in particular to a catch device and a shell liner for use in a medical imaging apparatus such as a magnetic resonance imaging apparatus.

Description of the Prior Art

Magnetic Resonance Imaging (MRI) is a modern medical imaging method, including nuclear magnetic resonance. Compared with other imaging devices, such as X-ray and CT, MRI can provide better contrast between different soft tissues.

The high performance and good application prospects of MRI systems promote the wide range of applications thereof, and continue to expand the market size thereof.

Currently, due to considerations relating to use, a variety of medical instruments are required to be simple and clean in appearance, so it is required to use a shell to cover each component therein to isolate those components from the outside. This can prevent devices within the medical instrument from being affected by outside influences, and can enhance the appearance of the medical instrument, and at the same time can avoid accidental damage to the devices within the medical instrument by an operator.

Due to the different requirements as to appearance, the shell of the medical instrument is not a completely integrated design, but is composed of multiple shell parts. In the existing medical instruments, the shell parts are usually connected by fixing elements, such as screws or rivets. However, this connection method causes difficulties when maintaining medical instruments, as time taken to remove the shell will be excessive.

Moreover, with regard to advanced large medical devices, such as MRI, it is desirable that the fixing elements on the surface of the shell should be not visible as far as possible, so as to avoid scratching or damage to the appearance caused by the projection of the fixing element. Moreover, in view of maintenance, the shell should be conveniently removable and mounted to facilitate the maintenance and repair. The requirements of both aspects cannot be achieved by a connection using fixing elements such as the above-described rivets or screws. Moreover, a method of connection involving too many fixing elements, such as the rivets or screws, will lead to distortion and deformation of the shell.

SUMMARY OF THE INVENTION

The present invention provides a catch device, a shell liner, a medical imaging apparatus and a magnetic resonance imaging apparatus to achieve a simple and firm connection between apparatus shells so as to meet requirements for a pleasing appearance, convenient application and maintenance.

A catch device, used for catching a first shell and a second shell, has an elastic arm that has a clamping portion, two bending portions located on two sides of the clamping portion, and two end portions formed by extension of the ends of the two bending portions away from the clamping portion, the two end portions being used for being fixed to a liner of the first shell, and at least one roller, the roller being rotatably sheathed on the clamping portion of the elastic arm and clamping an edge of the second shell to the liner of the first shell by using an elastic force of the elastic arm, and an axial direction of the roller being parallel to the liner of the first shell and the edge of the second shell.

Furthermore, in an embodiment wherein the number of the rollers is one, the roller is sheathed in the middle of the clamping portion, and the two sides of the roller have limit structures for preventing the roller from sliding along the elastic arm.

Furthermore, the clamping portion in this embodiment has a straight portion and two curved portions disposed symmetrically, and the roller is sheathed on the straight portion, and the two curved portions form the limit structure.

Furthermore, in an embodiment wherein the number of the rollers is two, the rollers are symmetrically sheathed to the clamping portion, and the two sides of each roller have limit structures for preventing the roller from sliding along the elastic arm.

Furthermore, the clamping portion is of a linear type, and each of the two sides of each roller sheathed to the linear-type clamping portion has a boss and/or a clasp as the limit structure.

In a further embodiment, the two end portions of the elastic arm are fixed to a limit member, and the limit member is fixed to the liner of the first shell through a fixed component.

A shell, for use in a medical imaging apparatus, has the catch device described as above.

A medical imaging apparatus has at least one first shell and at least one second shell, and the catch device described as above.

A magnetic resonance imaging apparatus, having at least one first shell and at least one second shell, further has the catch device described as above.

It can be seen from the above solution that, in the catch device and the shell liner, the medical imaging apparatus and the magnetic resonance imaging apparatus using the catch device of the present invention, at the liner of the first shell, by contacting the peripheral surface of the roller sheathed on the elastic arm with the edge of the second shell or a region adjacent to the edge of the second shell and by means of the symmetrically shaped elastic arm, the force that is applied to the elastic arm by the second shell via the roller is symmetrically applied to the elastic arm, so as to tightly catch the first shell and the second shell, while ensuring the even stress on the elastic arm and prolonging the service life of the elastic arm. Meanwhile, since the catch device is arranged in the shell liner, in view from the outer surface, the connection of the device shell has a pleasing and simple appearance. The catch device of the present invention has a simple structure, achieves a simple and firm connection between device shells, and meets requirements for a pleasing appearance and convenient application and maintenance.

In an embodiment using one roller in the present invention, due to the limit from the limit structure, the roller can only be located in the middle of the elastic arm, and when catching the first shell and a second shell, the force applied by the second shell to the roller can be symmetrically transferred to the clamping portion and the two bending portions of the elastic arm, so as to further achieve the even stress on the elastic arm to achieve stable clamping. In this embodiment, the roller is sheathed on the straight portion, so that the roller can roll around the straight portion as the axis, thereby achieving the minimum friction between the roller and the elastic arm. The two symmetrically arranged curved portions on the one hand achieve the purpose of limiting sliding of the roller along the elastic arm, and on the other hand can transfer the force applied to the roller by the second shell to the two bending portions when the first shell and a second shell are caught, thereby achieving the even stress on the elastic arm.

In the embodiment using two rollers in the present invention, the limit structure symmetrically limits the two rollers on the clamping portion, and when catching the first shell and a second shell, the force applied by the second shell to the two rollers can be symmetrically and uniformly transferred to the clamping portion and the two bending portions of the elastic arm, so as to further achieve the even stress on the elastic arm to achieve stable clamping. The limit structure uses a boss and/or a clasp, thereby achieving the goal of simplicity.

Figure 1:
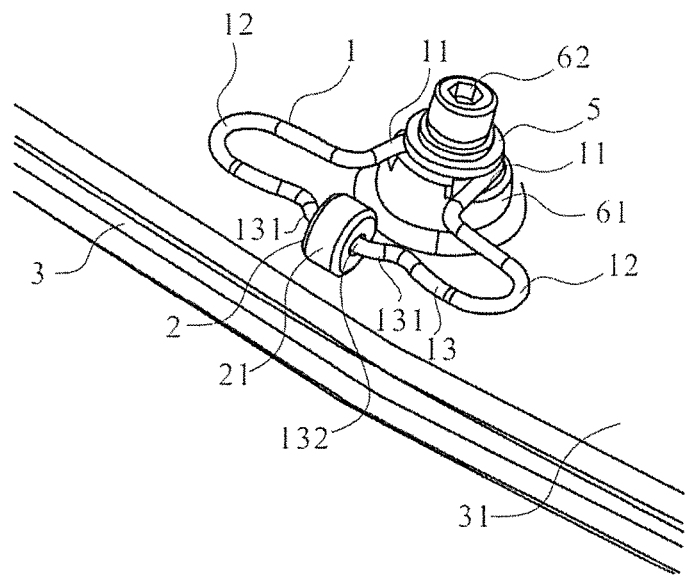
FIG. 1 is a schematic view of a first embodiment of a catch device in accordance with the present invention.

In the drawings, the following reference numbers are used:

1 Elastic arm
11 End portion
12 Bending portion
13 Clamping portion
131 Curved portion
132 Straight portion
14 Clasp
2 Roller
21 Peripheral surface
3 First shell
31 Liner
4 Second shell
41 Edge
5 Limit member
61 Pipe nut
62 Bolt

DESCRIPTION OF THE PREFERRED EMBODIMENTS

In an embodiment of the present invention, a catch device is provided for catching a first shell and a second shell, comprising an elastic arm and at least one roller. The elastic arm has a clamping portion, two bending portions located on two sides of the clamping portion, and two end portions formed by extension of the ends of the two bending portions away from the clamping portion, both the two end portions being used for being fixed to a liner of the first shell. The roller is rotatably sheathed on the clamping portion of the elastic arm and clamps an edge of the second shell to the liner of the first shell by using an elastic force of the elastic arm, and an axial direction of the roller is parallel to the liner of the first shell and the edge of the second shell.

In the catch device of the present invention, at the liner of the first shell, by contacting the peripheral surface of the roller sheathed on the elastic arm with the edge of the second shell or a region adjacent to the edge of the second shell and by means of the symmetrically shaped elastic arm, the force which is applied to the elastic arm by the second shell via the roller is symmetrically applied to the elastic arm, so as to tightly catch the first shell and the second shell, while ensuring the even stress on the elastic arm and prolonging the service life of the elastic arm. Meanwhile, since the catch device is arranged in the shell liner, in view from the outer surface, the connection of the device shell is aesthetically pleasing and simple. The catch device of the present invention has a simple structure, achieves a simple and firm connection between device shells, and meets requirements for a pleasing appearance and convenient application and maintenance.

The catch device of the present invention will be described in detail below in conjunction with two particular embodiments. In the first embodiment, the number of the rollers is one, the roller is sheathed in the middle of the clamping portion, and the two sides of the roller have limit structures for preventing the roller from sliding along the elastic arm; the clamping portion has a straight portion and two curved portions disposed symmetrically; and the roller is sheathed on the straight portion, and the two curved portions form the limit structure. In the second embodiment, the number of the rollers is two, the rollers are symmetrically sheathed to the clamping portion, and the two sides of each roller have limit structures for preventing the roller from sliding along the elastic arm. The clamping portion is of a linear type, and each of the two sides of each roller sheathed to the linear-type clamping portion has a boss and/or a clasp as the limit structure. In addition, in the second embodiment, the clamping portion and the two bending portions are integrally formed, or the clamping portion and the two bending portions are connected and fixed in an assembly relationship. In the second embodiment, a boss or a clasp as a limit structure is provided on one side of the two bending portions close to the clamping portion; bosses or clasps as a limit structure are provided on two sides of the clamping portion close to the two bending portions; and each roller is located between two adjacent limit structures.

The First Embodiment

Figure 2:
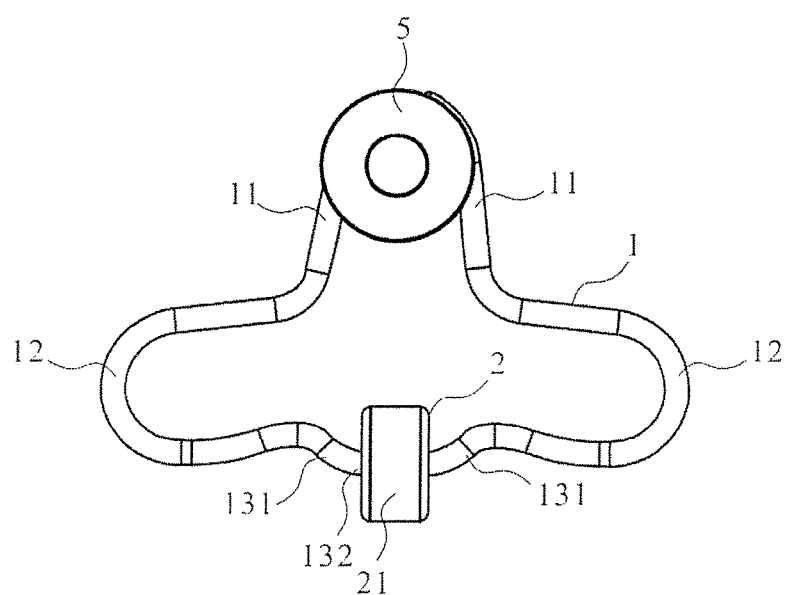
FIG. 2 is a schematic top view of an elastic arm and a roller in the first embodiment of a catch device in accordance with the present invention.
Figure 3:
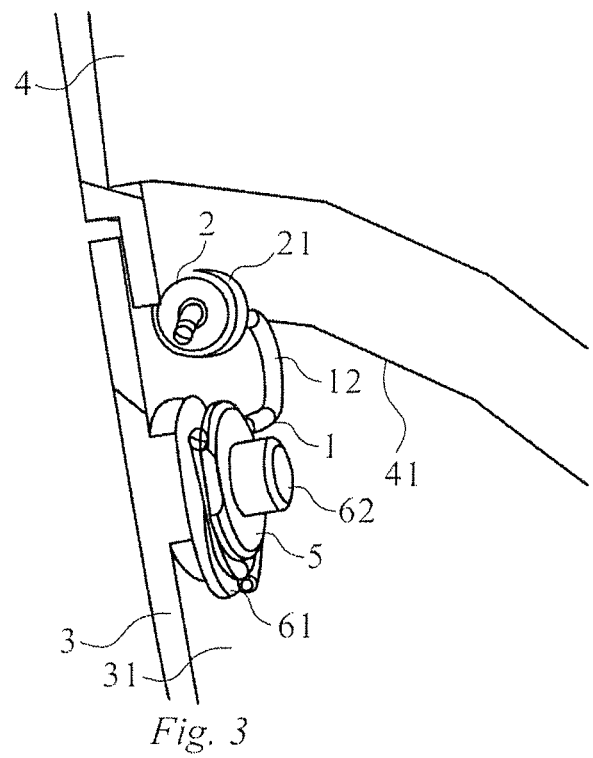
FIG. 3 is a structural schematic view of the first embodiment of a catch device catching shells in accordance with the present invention.
Figure 4:
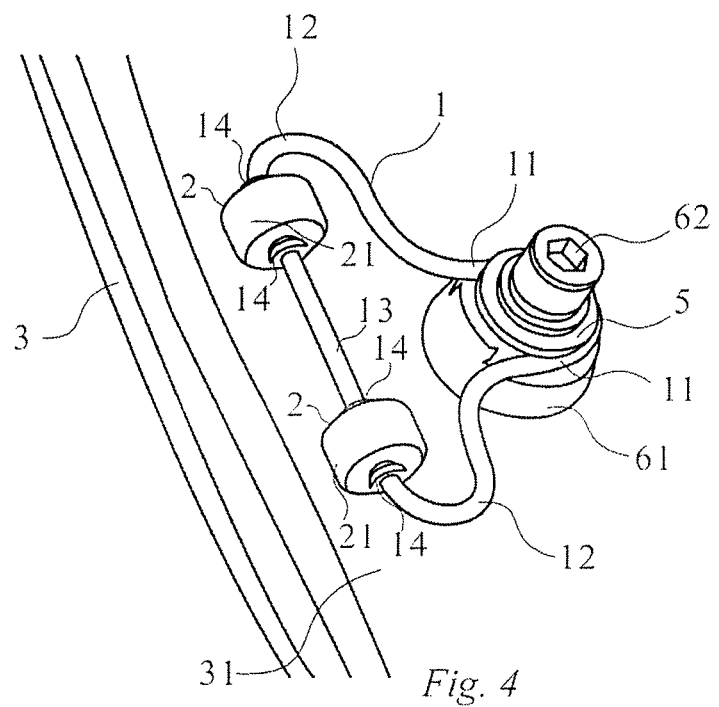
FIG. 4 is a schematic view of a second embodiment of a catch device in accordance with the present invention.

FIGS. 1-3 are structural schematic views of the first embodiment of a catch device of the present invention. As shown combined in FIGS. 1-3, the catch device of the first embodiment comprises an elastic arm 1 and a roller 2. The end portion 11 of the elastic arm 1 is fixed to the liner 31 of the first shell 3. The number of rollers 2 is one, the roller 2 is rotatably sheathed on the elastic arm 1, and the roller 2 clamps the edge 41 of the second shell 4 on the liner 31 of the first shell 3 using the elastic force of the elastic arm 1. The elastic arm 1 has two end portions 11, two bending portions 12 respectively close to the two end portions 11, and a clamping portion 13 located between the two bending portions 12, wherein the two end portions 11 are symmetrically arranged, the two bending portions 12 are symmetrically arranged, and two bending portions 12 are U-shaped with the arc portion of the U profile facing toward the outside, as shown in FIG. 2. The roller 2 is sheathed on the clamping portion 13, and the axial direction of the roller 2 is parallel to the liner 31 of the first shell 3 and to the edge 41 of the second shell 4, as shown in FIGS. 1 and 3. The axial direction of the roller 2 is parallel to the liner 31 of the first shell 3 and to the edge 41 of the second shell 4, such that in the clamping process the peripheral surface 21 of the roller 2 can touch the edge of the second shell 4 and then further follow the rolling of the roller 2 to clamp the second shell 4 between the liner 31 of the first shell 3 and the roller 2, thereby achieving the clamping for the second shell 4.

In particular, as shown in FIG. 2, the roller 2 is sheathed in the middle of the clamping portion 13, and each of the two sides of the roller 2 has a limit structure for preventing the roller 2 from sliding along the elastic arm 1. The clamping portion 13 has two symmetrically arranged curved portions 131 respectively formed by extension of the two bending portions 12 away from the two end portions 11; the two curved portions 131 extend in the direction away from the end portion 11 and in the direction to which the two curved portions 131 are close to each other, and are connected with each other to form a straight portion 132; the roller 2 is sheathed on the straight portion 132, the two curved portions 131 constitute the limit structure, so that the two curved portions 131 limit the sliding of the roller 2 along the elastic arm 1, and further the roller 2 can only be located in the middle of the elastic arm 1; and when catching the first shell 3 and a second shell 4, the force applied to the roller 2 by the second shell 4 can be symmetrically transferred to the clamping portion 13 and two bending portions 12 of the elastic arm 1, thereby achieving the even stress on the elastic arm 1 to achieve stable clamping.

As shown in FIG. 2, the two end portions 11 of the elastic arm 1 are fixed to a limit member 5, and the limit member 5 is fixed to the liner 31 of the first shell 3 through a fixed component. As a particular embodiment, the limit member 5 is a washer; the fixed component comprises a pipe nut 61 fixed to the liner 31 of the first shell 3 and a bolt 62 arranged passing through the washer and screwed in the pipe nut 61; and by way of the screwing of the bolt 62 into the pipe nut 61, the washer is fixed to the liner 31 of the first shell 3, thereby achieving the fixing of the catch device to the liner 31 of the first shell 3. As another embodiment, a through-hole may also be punched on the first shell 3, the washer is disposed on the liner 31 side of the through-hole through a pipe pad, and the pipe pad and the washer are fixed by the fitting between the bolt and the nut, thereby achieving the fixing of the catch device to the liner 31 of the first shell 3. Certainly, the pipe pad, the through-hole and the first shell 3 may be integrally designed, or the pipe nut 61 and the first shell 3 are integrally designed, so as to achieving the fixing of the catch device to the liner 31 of the first shell 3. In addition to the above fixing means of the catch device to the liner 31 of the first shell 3, there are many other fixing means, such as welding, which will not be listed here.

As shown in FIG. 3, as a particular embodiment, the second shell 4 and the first shell 3 are both shells of a medical imaging apparatus and/or a magnetic resonance imaging apparatus, and the second shell 4 has been mounted on the medical imaging apparatus and/or the magnetic resonance imaging apparatus. Here, when the first shell 3 and the second shell 4 are connected by clamping, the liner 31 of the first shell 3 is moved toward the position to be mounted and toward the mounting position, then since the axial direction of the roller 2 is parallel to the liner 31 of the first shell 3 and to the edge 41 of the second shell 4, the peripheral surface 21 of the roller 2 of the catch device fixed in the liner 31 of the first shell 3 first touches the edge 41 of the second shell 4. Here, the mounting position of the catch device in the liner 31 of the first shell 3 should ensure the edge 41 of the second shell 4 touches the outer half peripheral surface 21 of the roller 2 away from the end portion 11 of the elastic arm 1, and when the first shell 3 is moving toward the mounting position, the edge 41 of the second shell 4 can apply a push force to the roller 2. Along with the movement of the first shell 3 toward the mounting position, the push force applied to the roller 2 by the edge 41 of the second shell 4 pushes the bending portion 12 of the elastic arm 1 to perform compressive deformation on the end portion 11 of the elastic arm 1; when the liner 31 of the first shell 3 touches the second shell 4, the edge 41 of the second shell 4 is located on the portion close to liner 31 of the first shell 3 of the outer half peripheral surface 21, of the roller 2 away from the end portion 11 of the elastic arm 1; and then under action of the resilient effect of the elastic arm 1, the elastic arm 1 tightly presses the edge 41 of the second shell 4 on the liner 31 of the first shell 3 through the roller 2, thereby achieving the clamping connection between the first shell 3 and the second shell 4.

In this embodiment, in the case that the elastic arm 1 is not affected by forces, the distance between the axis of the roller 2 and the liner 31 of the first shell 3 should be greater than the thickness of the edge 41 of the second shell 4, and the distance between the peripheral surface 21 of the roller 2 and the liner 31 of the first shell 3 shall be less than the thickness of the edge 41 of the second shell 4. The axis of the roller 2 should be parallel to the edge 41 of the second shell 4 that the roller 2 touches.

The Second Embodiment

Figure 5:
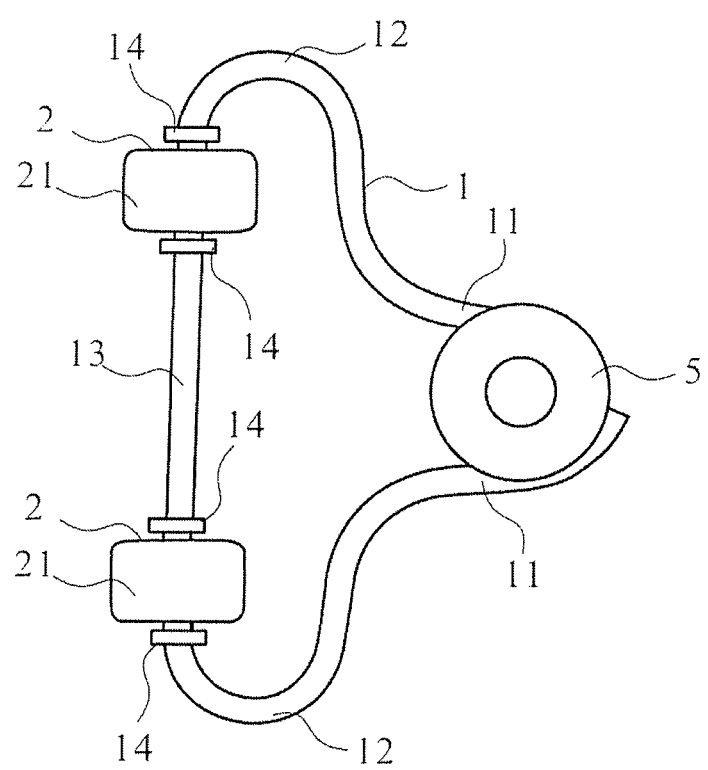
FIG. 5 is a schematic top view of an elastic arm and a roller in the second embodiment of a catch device in accordance with the present invention.

FIGS. 4-7 are structural schematic views of the second embodiment of a catch device of the present invention. As shown combined in FIGS. 4-7, the catch device of the second embodiment comprises an elastic arm 1 and a roller 2. The end portion 11 of the elastic arm 1 is fixed to the liner 31 of the first shell 3. The number of rollers 2 is two, the rollers 2 are symmetrically and rotatably sheathed on the elastic arm 1, and the two rollers 2 clamp the edge 41 of the second shell 4 on the liner 31 of the first shell 3 using the elastic force of the elastic arm 1. The elastic arm 1 has two end portions 11, two bending portions 12 respectively close to the two end portions 11, and a clamping portion 13 located between the two bending portions 12, wherein the two end portions 11 are symmetrically arranged, the two bending portions 12 are symmetrically arranged, and two bending portions 12 are U-shaped with the arc portion of the U profile facing toward the outside, as shown in FIG. 5. The rollers 2 are symmetrically sheathed on the clamping portion 13, each of the two sides of each roller 2 has a limit structure for preventing the roller 2 from sliding along the elastic arm 1, and the axial direction of the roller 2 is parallel to the liner 31 of the first shell 3 and to the edge 41 of the second shell 4, as shown in FIGS. 1 and 3. The axial direction of the roller 2 is parallel to the liner 31 of the first shell 3 and to the edge 41 of the second shell 4, such that in the clamping process, the peripheral surface 21 of the roller 2 can touch the edge of the second shell 4 and then further follow the rolling of the roller 2 to clamp the second shell 4 between the liner 31 of the first shell 3 and the roller 2, thereby achieving the clamping for the second shell 4.

In particular, as shown in FIG. 5, the clamping portion 13 is of a linear type, and is formed by the extension of the two bending portions 12 away from the two end portions 11. The two rollers 2 are symmetrically sheathed on the linear-type clamping portion 13. The elastic arm 1 on two sides of the roller 2 is provided with a clasp 14, and the clasp 14 constitutes the limit structure to limit the roller 2 to slide along the elastic arm 1. In addition, a boss may replace the clasp 14 to serve as the limit structure. In this way, the clamping portion 13 and the bending portion 12 are designed as integrally formed.

Alternatively, the clamping portion 13 and the bending portion 12 are designed separately, and the clamping portion 13 and the two bending portions 12 are connected and fixed in an assembly relationship. The portion of the two bending portions 12 close to the clamping portion 13 is provided with a clasp 14. The clamping portion 13 is of a linear type, and the portions of the clamping portion 13 close to the two bending portions 12 are each provided with a clasp 14. The two rollers 2 are respectively mounted between the clamping portion 13 and the two bending portions 12, and the ends of the two bending portions 12 close to the clamping portion 13 and two ends of the clamping portion 13 respectively close to the two bending portions 12 are arranged passing through the axle of the roller 2, and the clasp 14 limits the sliding of roller 2 along the elastic arm 1.

In the second embodiment, the limit structure symmetrically limits the two rollers 2 on the clamping portion 13, and when catching the first shell 3 and a second shell 4, the force applied by the second shell 4 to the two rollers 2 can be symmetrically and evenly transferred to the clamping portion 13 and the two bending portions 12 of the elastic arm 1, so as to further achieve the even stress on the elastic arm 1 to achieve stable clamping. The limit structure uses a boss and/or a clasp, thereby achieving the aim of simplicity.

As shown in FIG. 5, the two end portions 11 of the elastic arm 1 are fixed to a limit member 5, and the limit member 5 is fixed to the liner 31 of the first shell 3 through a fixed component. As a particular embodiment, the limit member 5 is a washer; the fixed component comprises a pipe nut 61 fixed to the liner 31 of the first shell 3 and a bolt 62 arranged passing through the washer and screwed in the pipe nut 61; and by way of the screwing of the bolt 62 into the pipe nut 61, the washer is fixed to the liner 31 of the first shell 3, thereby achieving the fixing of the catch device to the liner 31 of the first shell 3. As another embodiment, a through-hole may also be punched on the first shell 3, the washer is disposed on the liner 31 side of the through-hole through a pipe pad, and the pipe pad and the washer are fixed by the fitting between the bolt and the nut, thereby achieving the fixing of the catch device to the liner 31 of the first shell 3. Certainly, the pipe pad, the through-hole and the first shell 3 may be integrally designed, or the pipe nut 61 and the first shell 3 are integrally designed, so as to achieve the fixing of the catch device to the liner 31 of the first shell 3. In addition to the above fixing means of the catch device to the liner 31 of the first shell 3, there are many other fixing means, such as welding, which will not be listed here.

Figure 6:
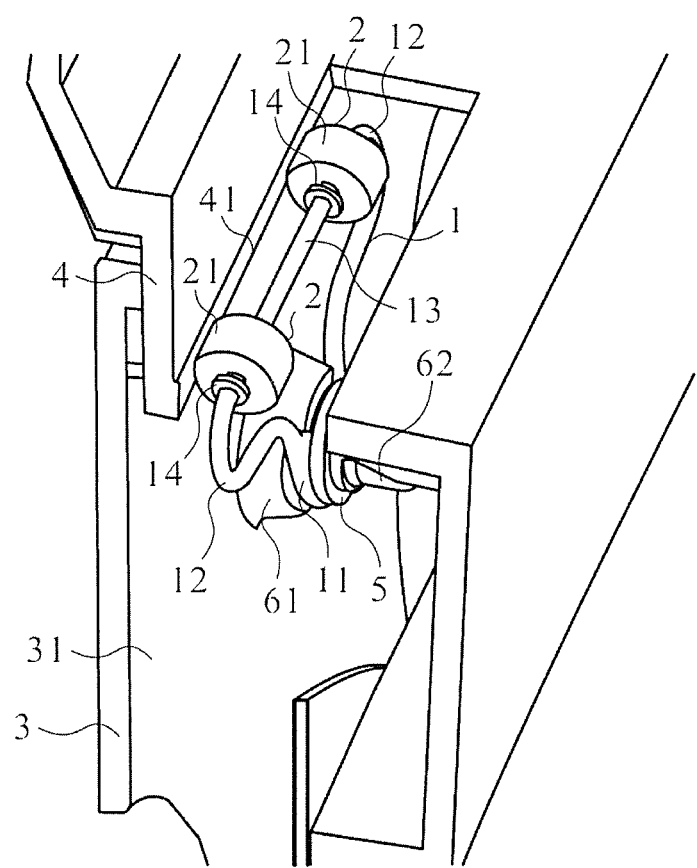
FIG. 6 is a first structural schematic view of the second embodiment of a catch device catching shells in accordance with the present invention.
Figure 7:
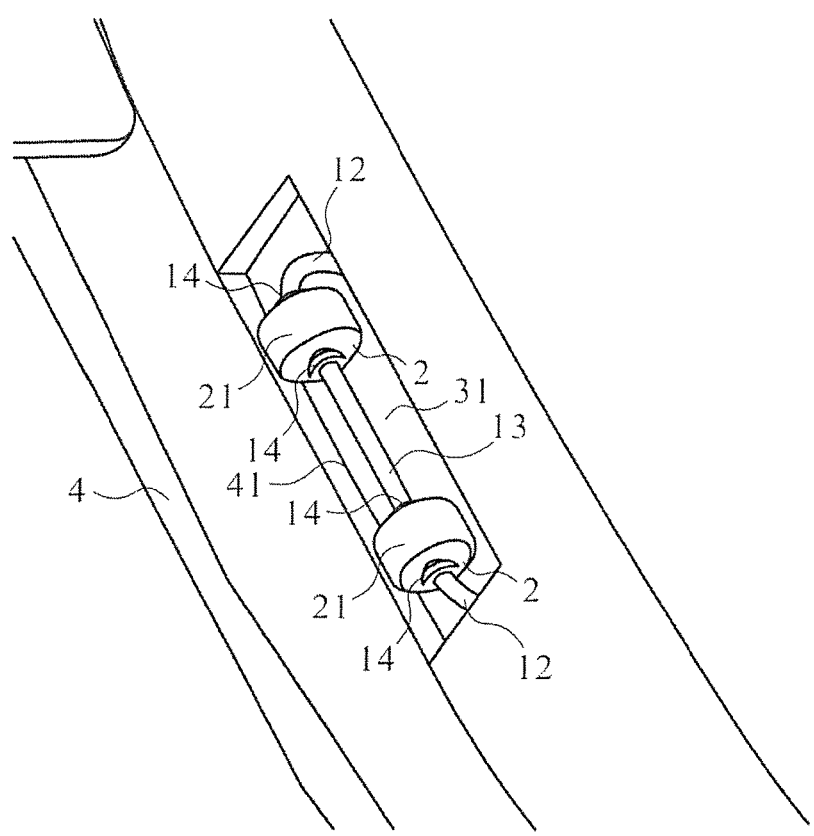
FIG. 7 is a second structural schematic view of the second embodiment of a catch device catching shells in accordance with the present invention.

As shown in FIGS. 6 and 7, as a particular embodiment, the second shell 4 and the first shell 3 are both shells of a medical imaging apparatus and/or a magnetic resonance imaging apparatus, and the second shell 4 has been mounted on the medical imaging apparatus and/or the magnetic resonance imaging apparatus. Here, when the first shell 3 and the second shell 4 are connected by clamping, the liner 31 of the first shell 3 is moved toward the position to be mounted and toward the mounting position, then since the axial direction of the roller 2 is parallel to the liner 31 of the first shell 3 and to the edge 41 of the second shell 4, both of the peripheral surfaces 21 of the two rollers 2 of the catch device fixed in the liner 31 of the first shell 3 first touch the edge 41 of the second shell 4. Here, the mounting position of the catch device in the liner 31 of the first shell 3 should ensure the edge 41 of the second shell 4 touches the outer half peripheral surface 21 of the roller 2 away from the end portion 11 of the elastic arm 1, and when the first shell 3 is moving toward the mounting position, the edge 41 of the second shell 4 can apply a push force to the roller 2. Along with the movement of the first shell 3 toward the mounting position, the push force applied to the two rollers 2 by the edge 41 of the second shell 4 pushes the two bending portions 12 of the elastic arm 1 to perform compressive deformation on the end portion 11 of the elastic arm 1; when the liner 31 of the first shell 3 touches the second shell 4, the edge 41 of the second shell 4 is located on the portion close to liner 31 of the first shell 3 of the outer half peripheral surface 21 of the two rollers 2 away from the end portion 11 of the elastic arm 1; and then under action of the resilient effect of the elastic arm 1, the elastic arm 1 tightly presses the edge 41 of the second shell 4 on the liner 31 of the first shell 3 through the two rollers 2, thereby achieving the clamping connection between the first shell 3 and the second shell 4.

In this embodiment, in the case that the elastic arm 1 is not affected by forces, the distance between the axes of the two rollers 2 and the liner 31 of the first shell 3 should be greater than the thickness of the edge 41 of the second shell 4, and the distance between the peripheral surfaces 21 of the two rollers 2 and the liner 31 of the first shell 3 shall be less than the thickness of the edge 41 of the second shell 4. The axes of the two rollers 2 should be parallel to the edge 41 of the second shell 4 that the rollers 2 touch.

The above two embodiments are for designs of one roller and two rollers. However, in addition to the above two embodiments, three or more rollers may be used in the present invention, the three or more rollers only needing to be symmetrically sheathed on the clamping portion 13 of the elastic arm 1, and in order to prevent the three or more rollers from transversely sliding along the elastic arm 1, the three or more rollers can be limited to the corresponding positions in the clamping portion 13, likewise the solutions in the first and/or second embodiment. The design of three or more rollers may have the same effect as those of the above two embodiments. The embodiment regarding three or more rollers may be designed according to the above two embodiments, which will not be mentioned again here.

In the present invention, one or more catch devices may be arranged in the liner of the first shell according to the shape and assembly/disassembly requirements of the first shell and the second shell, so as to satisfy the requirements of convenient assembly and disassembly.

The embodiments of the present invention provide a shell liner which is used for a medical imaging apparatus and mainly used for a peripheral shell of a medical imaging apparatus, the shell liner comprising the catch device disclosed above. Using this shell liner, the peripheral shell of the medical imaging apparatus can be conveniently assembled and disassembled.

The embodiments of the present invention further provide a medical imaging apparatus which is provided with at least one first shell and at least one second shell and further comprises the catch device disclosed above.

The embodiments of the present invention further provide a magnetic resonance imaging apparatus which is provided with at least one first shell and at least one second shell and further includes the catch device disclosed above.

The medical imaging apparatus and magnetic resonance imaging apparatus provided by the embodiments of the present invention especially aim at the problems, such as inconvenient assembly and disassembly and inconvenient maintenance and repair, of the existing large medical apparatus shells, and the arrangement of the above catch device in the liner of the first shell can achieve a simple and firm connection between the shells of the medical imaging apparatus and the magnetic resonance imaging apparatus so as to meet requirements for a pleasing appearance and convenient application and maintenance.

Although modifications and changes may be suggested by those skilled in the art, it is the intention of the inventors to embody within the patent warranted hereon all changes and modifications as reasonably and properly come within the scope of their contribution to the art.

We claim as our invention:

1. A catch device, for catching a first shell and a second shell, the catch device comprising:
    an elastic arm, having a clamping portion, two bending portions located on two sides of the clamping portion, and two end portions formed by extension of the ends of the two bending portions away from the clamping portion, the two end portions being fixed to a liner of the first shell and producing a clamping force;
    one roller, said one roller being rotatably sheathed on the clamping portion of the elastic arm in a middle of said clamping portion, and clamping an edge of the second shell to the liner of the first shell by using an elastic force of the elastic arm, and an axial direction of the roller being parallel to the liner of the first shell and the edge of the second shell so that said one roller rolls on said liner to transfer said clamping force via the liner to the first shell, so as to clamp said first shell against said second shell; and
    said clamping portion comprising a straight portion and two curved portions disposed symmetrically relative to said straight portion, with said one roller being sheathed on said straight portion and said two curved portions forming respective limit structures that prevents said one roller from sliding along said elastic arm while still allowing transfer of said clamping force to said first shell.

2. The catch device as claimed in claim 1, wherein:
    the two end portions of the elastic arm are fixed to a mount; and
    the mount is fixed to the liner of the first shell through a fixed component.

3. An apparatus shell assembly, comprising:
    a first shell and a second shell;
    an elastic arm, having a clamping portion, two bending portions located on two sides of the clamping portion, and two end portions formed by extension of the ends of the two bending portions away from the clamping portion, the two end portions being fixed to a liner of the first shell and producing a clamping force;
    one roller, said one roller being rotatably sheathed on the clamping portion of the elastic arm in a middle of said clamping portion, and clamping an edge of the second shell to the liner of the first shell by using an elastic force of the elastic arm, and an axial direction of the roller being parallel to the liner of the first shell and the edge of the second shell so that said one roller rolls on said liner to transfer said clamping force via the liner to the first shell, so as to clamp said first shell against said second shell; and
    said clamping portion comprising a straight portion and two curved portions disposed symmetrically relative to said straight portion, with said one roller being sheathed on said straight portion and said two curved portions forming respective limit structures that prevents said one roller from sliding along said elastic arm while still allowing transfer of said clamping force to said first shell.

4. An apparatus shell assembly as claimed in claim 3, wherein:
    the two end portions of the elastic arm are fixed to a mount; and
    the mount is fixed to the liner of the first shell through a fixed component.

* * * * *